(12) United States Patent
Fisher et al.

(10) Patent No.: US 9,763,697 B2
(45) Date of Patent: Sep. 19, 2017

(54) ANTI-INFECTIVE SPINAL ROD WITH SURFACE FEATURES

(75) Inventors: Michael A. Fisher, Middleboro, MA (US); Paul Birkmeyer, Marshfield, MA (US); Hassan Serhan, South Easton, MA (US); Jeffrey Sutton, Medway, MA (US); Uri Herzberg, Bridgewater, NJ (US); Iksoo Chun, Princeton, NJ (US); Raymond S. Shissias, Iselin, NJ (US)

(73) Assignee: DePuy Synthes Products, Inc.

( * ) Notice: Subject to any disclaimer, the term of this patent is extended or adjusted under 35 U.S.C. 154(b) by 1367 days.

(21) Appl. No.: 12/336,055

(22) Filed: Dec. 16, 2008

(65) Prior Publication Data

US 2010/0152777 A1 Jun. 17, 2010

(51) Int. Cl.
*A61B 17/70* (2006.01)

(52) U.S. Cl.
CPC ........ *A61B 17/7032* (2013.01); *A61B 17/701* (2013.01)

(58) Field of Classification Search
CPC ............ A61B 17/7032; A61B 17/7034; A61B 17/7001; A61B 17/7002; A61B 17/702
USPC ............. 606/246, 264–279, 300–321, 60–68
See application file for complete search history.

(56) References Cited

U.S. PATENT DOCUMENTS

| | | |
|---|---|---|
| 5,268,178 A | 12/1993 | Calhoun |
| 5,281,222 A | 1/1994 | Allard |
| 5,281,419 A | 1/1994 | Tuan |
| 5,312,402 A | 5/1994 | Schlapfer |
| 5,423,818 A | 6/1995 | Van Hoeck |
| 5,476,462 A | 12/1995 | Allard |
| 5,486,174 A | 1/1996 | Fournet-Fayard |
| 5,552,102 A | 9/1996 | Kragle |
| 5,554,157 A * | 9/1996 | Errico et al. ............ 606/264 |
| 5,672,176 A | 9/1997 | Biedermann |
| 6,264,936 B1 | 7/2001 | Sawan |
| 6,338,904 B1 | 1/2002 | Patnark |
| 6,514,517 B2 | 2/2003 | Jamiolkowski |
| 6,575,945 B2 | 6/2003 | Prosl |
| 6,582,719 B2 | 6/2003 | Modak |
| 6,596,338 B2 | 7/2003 | Scott |
| 6,706,024 B2 | 3/2004 | Modak |
| 6,746,773 B2 | 6/2004 | Llanus |
| 6,770,075 B2 | 8/2004 | Howland |
| 6,843,784 B2 | 1/2005 | Modak |
| 6,887,270 B2 | 5/2005 | Miller |
| 7,175,611 B2 | 2/2007 | Mitchnick |
| 7,226,612 B2 | 6/2007 | Sohier |
| 7,270,665 B2 | 9/2007 | Morrison |

(Continued)

FOREIGN PATENT DOCUMENTS

| | | |
|---|---|---|
| WO | WO 9714447 | 4/1997 |
| WO | 03023401 | 3/2003 |

(Continued)

*Primary Examiner* — Ellen C Hammond
*Assistant Examiner* — Christina Negrellirodrigue

(57) ABSTRACT

Mechanical modifications to a spinal rod that will enable the rod to accept various coating technologies in such a way that the spinal construct's biomechanical performance is not compromised. These modifications preserve construct biomechanics in the presence of a coating and increase the bactericidal payload of an anti-infective spinal rod coating.

3 Claims, 5 Drawing Sheets

(56) References Cited

U.S. PATENT DOCUMENTS

| | | |
|---|---|---|
| 7,435,256 B2 | 10/2008 | Stenzel |
| 8,551,171 B2 * | 10/2013 | Johnson et al. ........... 623/17.11 |
| 2002/0058942 A1 | 5/2002 | Biedermann |
| 2002/0193879 A1 | 12/2002 | Seder |
| 2003/0055426 A1 | 3/2003 | Carbone |
| 2003/0147960 A1 | 8/2003 | Lin |
| 2003/0229319 A1 | 12/2003 | Mitchnick |
| 2004/0099762 A1 | 5/2004 | Shiga |
| 2004/0137065 A1 | 7/2004 | Vogt |
| 2004/0142013 A1 | 7/2004 | Rubsamen |
| 2004/0143264 A1 | 7/2004 | McAfee |
| 2004/0249441 A1 | 12/2004 | Miller |
| 2004/0267260 A1 * | 12/2004 | Mack et al. .................... 606/61 |
| 2005/0014151 A1 | 1/2005 | Textor |
| 2005/0159805 A1 | 7/2005 | Weber |
| 2005/0197634 A1 | 9/2005 | Raad |
| 2005/0277922 A1 * | 12/2005 | Trieu ................ A61B 17/7031 606/257 |
| 2006/0036251 A1 * | 2/2006 | Reiley ............... A61B 17/1615 606/301 |
| 2006/0041259 A1 * | 2/2006 | Paul et al. ...................... 606/61 |
| 2006/0211952 A1 * | 9/2006 | Kennedy, II .................. 600/585 |
| 2006/0247638 A1 | 11/2006 | Trieu |
| 2007/0093814 A1 | 4/2007 | Callahan, II |
| 2007/0156143 A1 | 7/2007 | Lancial |
| 2007/0190230 A1 | 8/2007 | Trieu |
| 2007/0191842 A1 | 8/2007 | Molz |
| 2007/0198088 A1 * | 8/2007 | Biedermann et al. ..... 623/17.11 |
| 2007/0224243 A1 | 9/2007 | Bayston |
| 2008/0033431 A1 * | 2/2008 | Jung et al. ...................... 606/61 |
| 2008/0086214 A1 | 4/2008 | Hardin |
| 2008/0183152 A1 | 7/2008 | Raad |
| 2009/0082810 A1 * | 3/2009 | Bhatnagar .......... A61B 17/7002 606/250 |
| 2009/0099610 A1 * | 4/2009 | Johnson et al. ........... 606/86 R |
| 2010/0082064 A1 | 4/2010 | Chun |

FOREIGN PATENT DOCUMENTS

| | | |
|---|---|---|
| WO | 2006118866 | 11/2006 |
| WO | 2007089984 | 8/2007 |

* cited by examiner

ANTI-INFECTIVE SPINAL ROD WITH SURFACE FEATURES

BACKGROUND OF THE INVENTION

Infection rates in spine surgery at typically below 3% whereas the rates in instrumented spine surgery range from 1-17%. The increased rate of infection is thought to be attributable to the use of synthetic biomaterials, longer procedure times, and more severe disease conditions that merit the placement of orthopedic implants.

It is strongly suspected that the presence of a synthetic biomaterial in a wound will increase the infection rate by two means—foreign body response and biofilm formation. Foreign body response is the body's reaction to any implanted material and typically creates a local hyper-immune response to the presence of a foreign material. Biofilm formation occurs when bacteria colonize a biomaterial surface and create a mucous layer to protect the colony from the host immune system. Once a bacterial biofilm has formed, it is unlikely that the immune system can resolve the infection.

One way to prevent device colonization is to apply a coating that prevents biofilm formation or has native anti-microbial properties. Unfortunately, applying coatings to spinal and orthopedic instrumentation is not trivial and most coatings fail to preserve some aspects of the device's mechanical function. Specific to spinal instrumentation, a coating must not compromise the mechanical nature of the implanted instrumentation. It has been demonstrated that most coatings degrade the strength of the device's mechanical interconnections.

The following documents are pertinent to this discussion: US Patent Publication 2004/0142013(Rubsamen); U.S. Pat. No. 5,476,462 (Zimmer); U.S. Pat. No. 5,281,222 (Zimmer); U.S. Pat. No. 5,312,402 (Synthes); U.S. Pat. No. 5,423,818 (Danek); U.S. Pat. No. 6,770,075 (Howland); US Patent Publication 2007/0093814 (Callahan); US Patent Publication 2004/0143264 (McAfee); PCT Patent Publication WO 2006/118866 (SDGI Holdings); U.S. Pat. No. 5,486,174 (Soprane); U.S. Pat. No. 7,270,665 (SDGI Holdings); US Patent Publication 20070156143 (Zimmer Spine); PCT Patent Publication WO2007089984 (Warsaw Orthopedic); PCT Patent Publication WO2003023401; U.S. Pat. No. 7,226,612 (Chienna); U.S. Pat. No. 7,175,611 (Mitchnick); U.S. Pat. No. 6,575,945 (Prosl); U.S. Pat. No. 6,596,338 (Scott); U.S. Pat. No. 6,706,024 (Modak); U.S. Pat. No. 6,514,517 (Jamiolkowski); U.S. Pat. No. 6,746,773 (Llanos); U.S. Pat. No. 6,338,904 (Patnaik); U.S. Pat. No. 6,264,936 (Sawan); US2003/0229319 (Mitchnik); US Patent Publication 2004/0137065 (Vogt); US Patent Publication 2004/0099762 (Zhang); US Patent Publication 2003/0147960 (Lin); U.S. Pat. No. 5,281,419 (Tuan); U.S. Pat. No. 5,268,178 (Calhoun).

SUMMARY OF THE INVENTION

The present invention describes ways to maintain the mechanical integrity of a coated spinal rod in a spinal construct by preserving the metal on metal contacts between the rod and a connecting device, such as a polyaxial screw.

The present invention describes mechanical modifications to a spinal rod that will enable the rod to accept various coating technologies in such a way that the spinal construct's biomechanical performance is not compromised. These modifications are advantageous in that they preserve construct biomechanics in the presence of the coating and increase the bactericidal payload of the anti-infective spinal rod coating.

Similarly, processing technologies are described that enable the additive, subtractive, and intra-operative selective processing and modification of coatings on a rod surface. Controlling the location, density, or pattern of the coating process can advantageously improve the coating efficacy while preserving the mechanical performance of the coated substrate, such as a spinal rod.

Thus, the present invention discloses rod surface features that preserve rod-screw mechanical interfaces, and surface features on spinal rods that elute anti-bacterial compounds.

The present invention further discloses spinal rod features that allow local anti-microbial depots and that preserve the mechanical function of a coated rod or enhance the biomechanical construct strength of a coated rod.

The present invention further discloses methods of coating a rod, and then removing aspects of that coating to preserve the rod's biomechanics. These include manufacturing arts that create surface features that enhance rod mechanics and enable larger coating payload, such as abrasive flows that create macro-surface depressions, abrasive flows that relieve edges of machined surface features, and burnishing processes that create local depressions without removing rod material.

Additional manufacturing arts include additive processes that create surface ridges: such as chemical vapor deposition, metal SLA addition, chemical precipitation, electrodeposition. Similarly, the invention contemplates surface features that act like electrostatic charge intensifiers (lightning rods) to preferentially accumulate or deflect coating materials that are applied in the presence of an electrical field. It would be advantageous that the modified surface be coated with particles such as particles that are created when polymer loaded with drug or drug solutions are atomized. Such atomization will maintain the surface "roughness" where as dip coating will obscure it. More over, if using electrostatic coating, the roughness of the rod can be specifically designed to create many "spikes" such spikes can serve to localize the drug at the tip of the spikes and prevent from drug or drug-polymer combination to be lodged at the recesses. In effect, the spikes work like small lighting rods and concentrate the charge and thereby bring an accumulation of the solution, which is charged with the opposite charge then the rod.

Coating removal around added features to enhance mechanical performance. Certain surface features can be added to the implant that are specifically present to enable partial removal of any subsequent coating. For example, a series of ridges could be added to the surface of the device, a coating added to the surface of the device, then a mechanical wiper or abrasion system could be used to remove the coating from the ridges only. Alternatively, the ridges could provide surface features that protect the coating during a mechanical removal process (i.e.—the coating would be preserved as a fillet of material where the ridge meets the rod surface).

One implant of the present invention may be created by adding a machined foil containing anti-microbial features/material to a spinal rod. Another implant of the present invention may be created by super-imposing a wire stent of material over a spinal rod to preserve mechanical performance.

In one embodiment, the implants of the present invention comprise local abrasive tabs within the screw heads to selectively remove rod coatings prior to engaging the screwhead set-screw.

In a related embodiment, the implants of the present invention comprise an abrasive agent present within the coating of the rod. This may be accomplished by adding calcium phosphate to the coating solution. As the coating solvent evaporates, the calcium phosphate precipitates and forms crystals. Those crystalline structures abrade the surface when the set screw is tightened, thereby removing the coating and allowing metal-metal interface to take place.

DETAILED DESCRIPTION OF THE INVENTION

Figure 1:
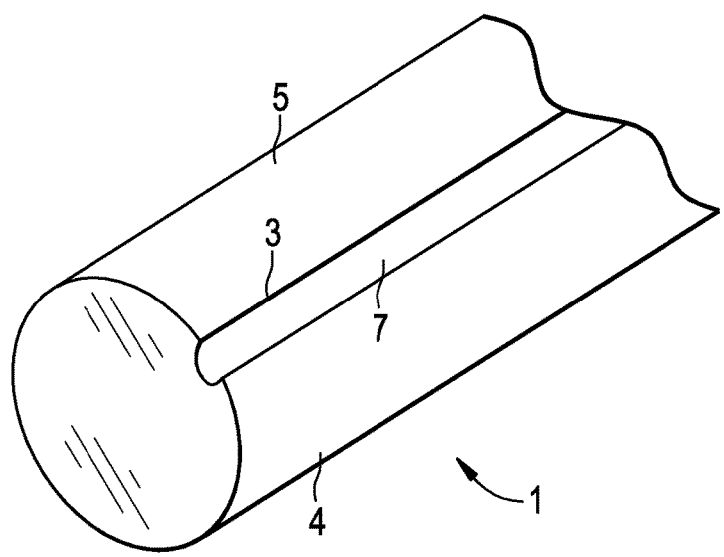
FIG. 1 discloses a perspective view of a rod of the present invention having an anti-infective coating in a longitudinal groove.

The present invention relates to the concept of an antibiotic coating on a grooved spinal rod. The invention being proposed is a mechanically modified spinal rod. The modifications are generally to the rod's surface features and cross-sectional geometry. In preferred embodiments of the present invention (FIG. 1), the spinal rod 1 has a groove 3 upon its outer surface 5, and the antibiotic 7 rests in the groove, so that spinal rod should maintain a substantially circular cross-sectional area if it is to interface with current screw system. Also preferably, the new features should not make the spinal rod prone to stress-risers, crack initiation, or material issues that will compromise the device's mechanical strength or fatigue life. Third, the anti-bacterial coating should be able to prevent bacterial colonization of the rod in the acute term. Finally, the rod surface should be able to accept a sufficient volume of anti-infective coating materials to deliver an effective payload of anti-bacterial active agent to the surrounding wound. Exemplary anti-bacterial agents include, but are not limited to, bactericidal compounds such as Irgacare MP™ triclosan by Ciba, Penicillin G, Ampicillin, Amoxicillin, Methicillin, Flucloxacillin, Carbenicillin, Piperacillin, Cefacetrile, Cefadroxil, Cefalexin, Cefaloglycin, Cefalonium, Cefaloridine, Cefalotin, Cefapirin, Cefatrizine, Cefazedone, Cefazaflur, Cefazolin, Cefradine, Cefroxadine, Ceftezole, Cefaclor, Cefamandole, Cefmetazole, Cefininox, Cefonicid, Ceforanide, Cefotiam, Cefprozil, Cefbuperazone, Cefuroxime, Cefuzonam, Cefixime, Cefmenoxime, Cefodizime, Cefoperazone, Cefotaxime, Cefpimizole, Cefpiramide, Cefpodoxime, Cefsulodin, Ceftazidime, Cefteram, Ceftibuten, Ceftiolene, Ceftizoxime, Ceftriaxone, Cefepime, Cefozopran, Cefpirome, Cefquinome, Ceftobiprole, Aztreonam, Biapenem, Doripenem, Ertapenem, Imipenem, Meropenem, Panipenem, Sulbactam, Tazobactam, Clavulanic acid, Colistin, Polymyxin B, Daptomycin, Vancomycin, Teicoplanin, Ramoplanin, Bacitracin, Fosfomycin, cycloserine, Chlortetracycline, Clomocycline, Demeclocycline, Doxycycline, Lymecycline, Meclocycline, Metacycline, Minocycline, Oxytetracycline, Penimepicycline, Rolitetracycline, Tetracycline, Streptomycin, Neomycin, Kanamycin, Hygromycin B, Spectinomycin, Paromomycin, Gentamicin, Verdamicin, Astromicin, Azidamfenicol, Chloramphenicol, Thiamphenicol, Florfenicol, Erythromycin, Spiramycin, Midecamycin, Oleandomycin, Roxithromycin, Josamycin, Troleandomycin, Clarithromycin, Azithromycin, Miocamycin, Rokitamycin, Dirithromycin, Flurithromycin, Telithromycin, Cethromycin, Clindamycin, Lincomycin, Pristinamycin, Quinupristin, Dalfopristin, Fusidic acid, Linezolid, Azithromycin, Clarithromycin, Dirithromycin, Erythromycin, Roxithromycin, Tulathromycin, Ciprofloxacin, and Levofloxacin.

Alternatively, the coating could be used to deliver antiviral compounds (like Avonex™ Interferon beta 1a by Biogen Idec), or anti-inflammatories (like curcumin ginger extract, corticosteroids, cyclo-oxygenase inhibitors, ibuprofen, etc.), or various biologic molecules (TGF-beta proteins like BMP-2 or GDF-5), or cancer prevention strategies (like Avastin by Genentech), or anti-scarring compounds (like integrin binding compounds like cyclic RGD's), or healing promoting compounds (like VEGF), or anti-vascular compounds (like anti-VEGF compounds like bevacizumab Avastin™ by Genentech/Roche).

An alternative embodiment contemplates the necessity of custom designed implants for specific patient anatomies. In such cases, the surface modifications could be selectively applied to a device's surface in order to accommodate the presence of a coating. In this embodiment, the location and need for an optimal mechanical surface would be predetermined and the appropriate means for applying the coating would be determined, then only those regions identified prior to surgery can be textured or modified to accommodate the therapeutic coating and specific anatomy of the patient.

In one preferred embodiment of the present invention, the rod surface modifications might include intermittent longitudinal striations (or "surface reliefs" or "surface recesses"). Such surface features preserve the substantially circular rod cross-sectional area while increasing the ability of the rod to hold an effective volume of coating material. The depth of the longitudinal surface reliefs should be on the order of microns so that the static mechanical properties of the rod are preserved. Preferably, the recessed portion has a depth of greater than 1 µm, more preferably between 1 µm and 1000 µm, most preferably between 1 µm and 100 µm. To preserve the rod's fatigue characteristics, the surface reliefs should be oriented parallel to the rod's principle axis—that is, they should be longitudinal recesses (as in FIG. 1). Now referring to FIGS. 2a and 2b, the recesses should also not have any sharp edges, and should display a rounded-off feature 9 at the start 11 and end 13 of the recess 3. By "blunting" the edges of the reliefs, it is possible to decrease local surface stress concentrations that might promote micro-crack formation and propagation (a key failure mode in fatigued metals). From a manufacturing perspective, abrasion or micro-machining a rod's surface prior to anodization, passivation, or chemical etching would enable these subsequent processes to "blunt" the edges and corners of the relief feature. One physical means to blunt the relief feature edges is abrasive flow processing (such as that described by ExtrudeHone in U.S. Pat. No. 5,552,102, the specification of which is hereby incorporated by reference in its entirety). Abrasive flow processing might be used to create surface reliefs that are devoid of edges and potential crack-initiating features (such surface reliefs would be barely perceptible to the eye due to the rounded nature of the resulting flow-eroded reliefs). Another means to create shallow surface reliefs that are devoid of corners and stress-raisers is the process of burnishing—the use of a hardened material to create plastic deformation at a material's surface without nominal material removal from the surface. The densified material within the burnished surface is actually stress-hardened and might improve the static and fatigue life of a spinal rod.

Figure 2A:
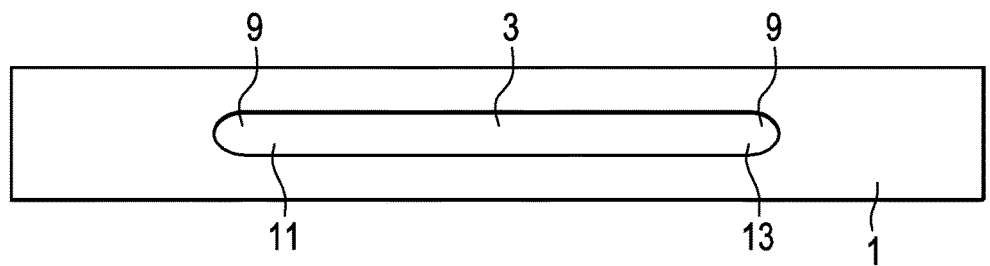
FIGS. 2a and 2b are cross-sections of rods of the present invention having a recess with rounded-off edges.
Figure 2B:
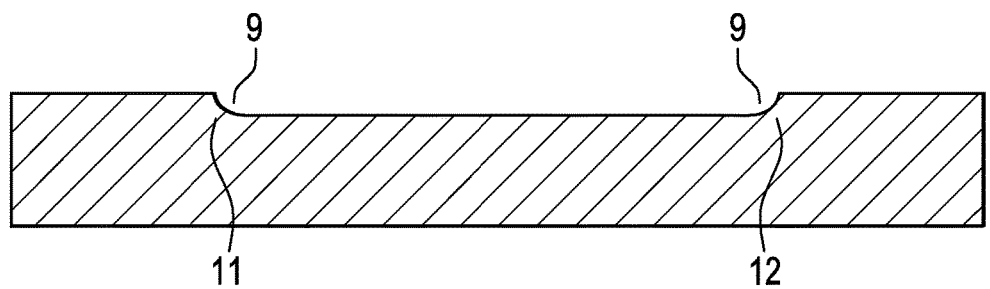

Therefore, in accordance with the present invention and FIG. 1, there is provided a spinal rod 1 having a substantially circular outer surface 5, the outer surface having a recessed portion 3 and a non-recessed portion 4, wherein the recessed portion contains an anti-microbial agent 7.

In some embodiments, the non-recessed portion comprises at least 50% of the outer surface, preferably at least 90% of the outer surface. The recessed portions of the surface can be long and continuous or short and intermittent.

Figure 3:
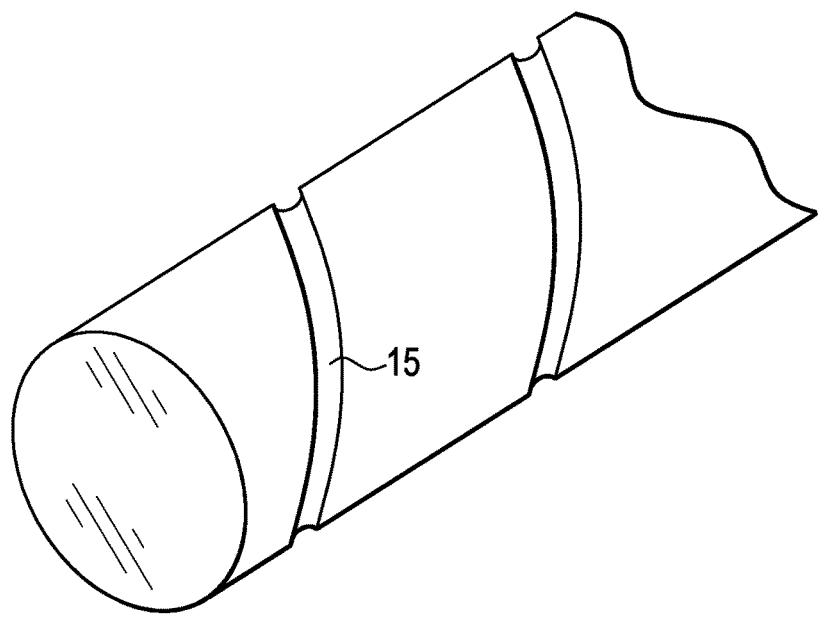
FIG. 3 discloses a perspective view of a rod of the present invention having an anti-infective coating in a helical groove.

In some embodiments, the recessed portion comprises at least one longitudinal recess, and more preferably a plurality of longitudinal recesses in order to provide more substantial radial coverage of the rod. Now referring to FIG. 3, in other embodiments, the recessed portion comprises at least one helical recess 15. The helical recess provides complete radial coverage of the rod. In some embodiments, the recessed portion has blunt edges created by either abrasive flow processing or by burnishing.

Figure 4:
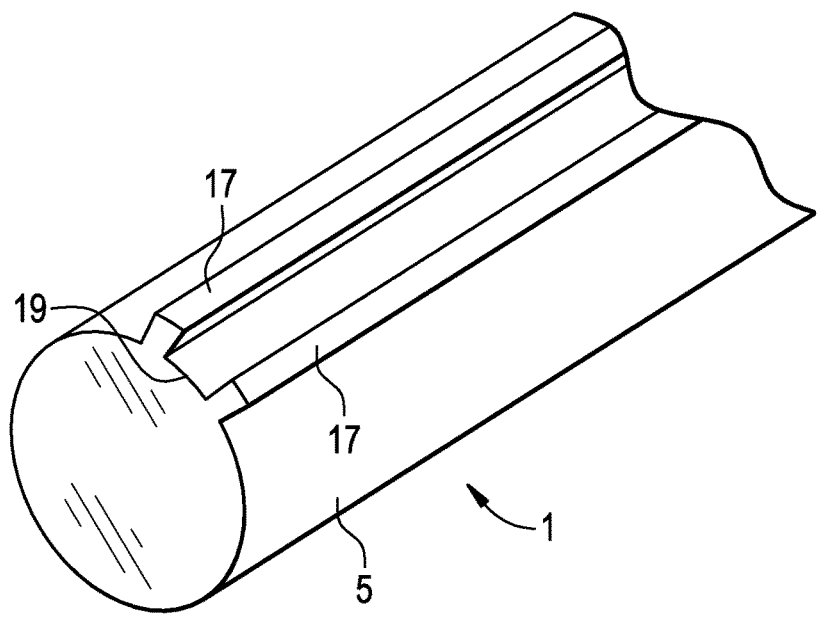
FIG. 4 discloses a perspective view of a rod of the present invention having an anti-infective coating between longitudinal ridges.

Now referring to FIG. 4, another rod surface modification might include the addition of longitudinal ridges 17. In these embodiments, the antibiotic is placed between the longitudinal ridges. Rather than removing material as in machined reliefs, adding material in ridges might preserve more mechanical rod strength while also preventing initiation/propagation of surface micro-cracks during fatigue. Such surface features would preserve the substantially circular rod cross-section, while presenting contact-stress-concentrators to the polyaxial screw cap. Such rod surface ridges would deform or "mash" into the screw, perhaps displacing the coating material with metal during micro surface deformation as the devices are compressed together. Also, applying a mechanical wiper to remove coating material from a ridged rod might be an effective way to more ideally remove coating material from the ridges in order to preserve bare-metal surface features. Manufacturing processes that add metal to a surface can be accomplished using metal SLA technologies, chemical vapor deposition, precipitation, cold annealing, and the like. Similarly, addition of ridges could enable a surface to hold more coating and payload than a flush surface.

Therefore, in accordance with the present invention and FIG. 4, there is provided a spinal rod 1 having a substantially circular outer surface 5, the outer surface having a ridged portion 17 and a non-ridged portion 19, wherein the non-ridged portion contains an anti-microbial agent (not shown).

In some embodiments, the ridged portion comprises at least 50% of the outer surface, preferably at least 90% of the outer surface.

In some embodiments, the ridged portion comprises at least one longitudinal ridge, preferably a plurality of longitudinal ridges.

In other embodiments, the ridged portion comprises at least one helical ridge.

In some embodiments, the ridged portion has a height of greater than 1 µm, more preferably between 1 µm and 1000 µm, most preferably between 1 µm and 100 µm In some embodiments, the ridged portion has blunt edges created by abrasive flow processing or by burnishing.

Figure 5:
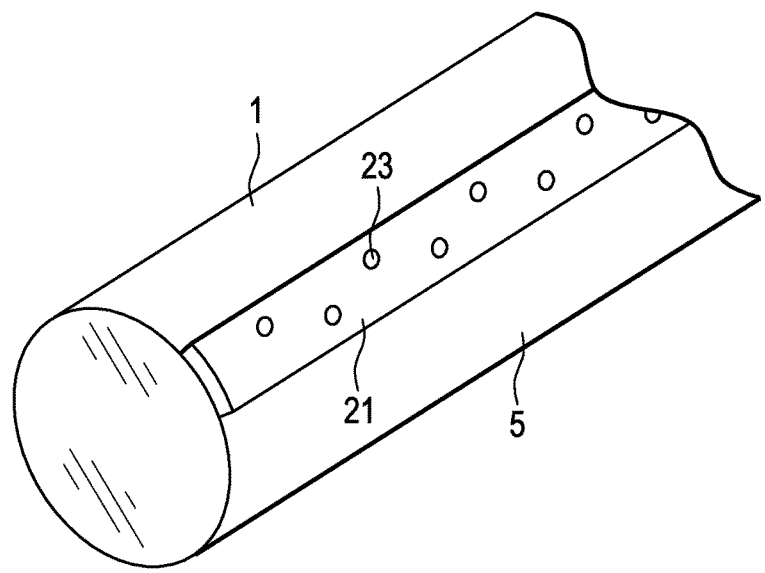
FIG. 5 discloses a perspective view of a rod contacting a separate metal foil having perforations containing the anti-infective.

Thin Foil: Now referring to FIG. 5, alternatively, a separate metal surface 21 can be added to a standard spinal rod 1. This added metal surface could be a coated foil that floats on the surface 5 of the standard rod. Sections of foil could be moved or removed within rod-screw interfaces. Alternatively, the metal foil could have perforations 23 or surface features that contain an anti-bacterial coating material. Such a perforated and coated metal foil might serve as a mechanical intermediary between the rod and screw seat features. Alternatively, one or more layers of foil could be selectively removed just prior to the application of a screw or attaching device in order to better preserve the mechanical connection. Because the foil contains the mechanical features that contain the coating material (more aptly called "micro-depots"), the rod does not have surface reliefs (stress raisers) or actual coating that serves as a slip-plane. When the foil-coated rod is seated into the screw during surgery, the foil would have various surface features to preserve metal-on-metal contact between the rod-foil-screw or rod-foil-set-screw. This concept might require the spinal rod outer diameter to be manufactured slightly smaller than current rods so the foil material can be accommodated within the tolerance stack-up. The foil can be made of any material, including metals, ceramics and plastics.

Figure 6:
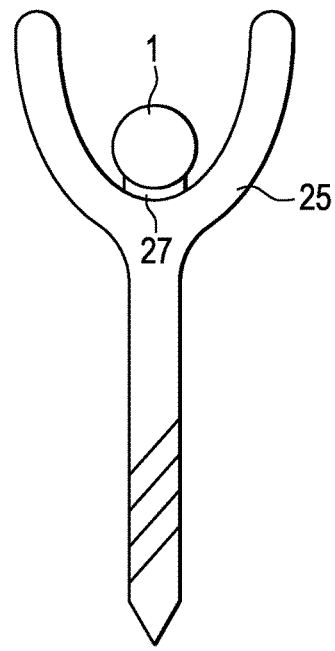
FIG. 6 discloses a bone anchor, rod and foil assembly wherein the foil is disposed between the rod and the recess of the bone anchor, wherein the foil comprises an antimicrobial agent.

Therefore, in accordance with the present invention and FIG. 6, there is provided a spinal stabilization system for use in a human spine, comprising:
  a) a bone anchor 25 having a recess for receiving a rod,
  b) a spinal rod 1 having a first end portion, wherein the first end portion of the spinal rod is received in the recess of the bone anchor, and
  c) a first foil 27 disposed between the rod and the recess of the bone anchor,
wherein the foil comprises an anti-microbial agent.

Figure 7:
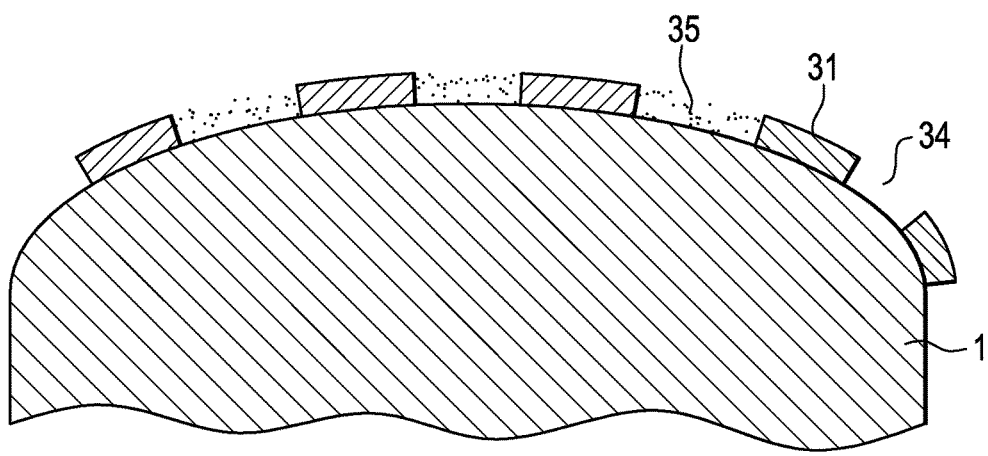
FIG. 7 discloses a rod-foil assembly wherein the foil comprises perforations, and the anti-microbial agent is present in the perforations.

Now referring to FIG. 7, in some embodiments, the first foil 31 comprises perforations, and the anti-microbial agent 35 is present in the perforations. In this embodiment, rod to bone anchor contact is maintained through the unperforated portion of the foil.

In other embodiments, the first foil comprises perforations that are free of the anti-microbial agent. In this embodiment, rod to bone anchor contact is maintained through the perforated portion of the foil.

In some embodiments, the first foil has a first surface, and the anti-microbial agent is present as a coating on the first surface of the foil.

In some embodiments, the system further comprises:
  d) a second foil (not shown) disposed between the rod and the recess of the bone anchor, wherein the second foil comprises an anti-microbial agent.

Figure 8:
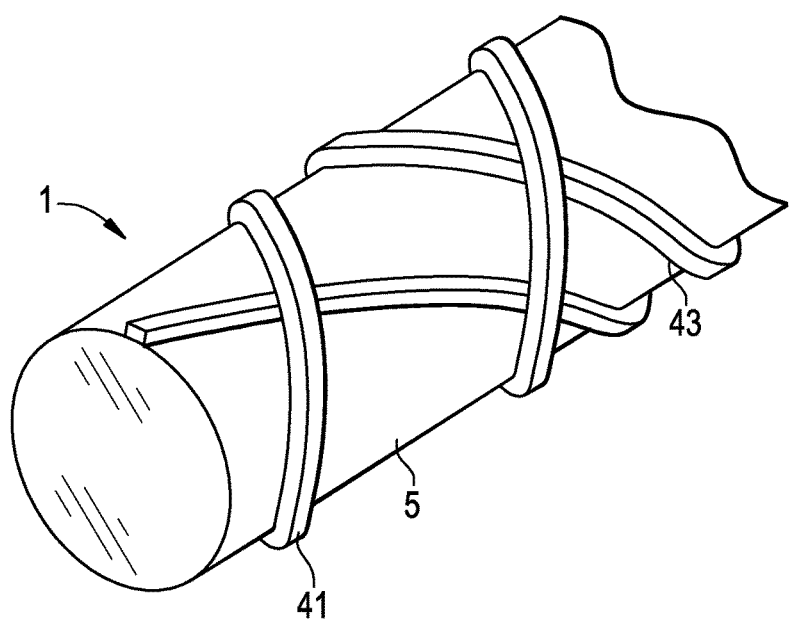
FIG. 8 discloses a spinal rod-stent assembly wherein the annular stent comprises an anti-microbial agent.

In an alternative embodiment, the foil could be considered as a wire mesh or stent that acts like the surface ridge features. In this situation, the wire foil stent would act like the previously described raised rod surface features. In fact, and now referring to FIG. 8, a thermally expanded foil stent 41 could be inserted over the outer surface 5 of a cooled spinal rod 1 to achieve a "foil coated rod" at operative temperature with extremely tight material tolerances. Once the stent cooled, it would have a tight fit with the rod. The benefit of this concept is that a foil stent would not contain any mechanical surface features that predispose a spinal rod to static or fatigue failure. The actual stent could be made from a material that is harder or softer than the rod and screw-seat materials. Exemplary hard materials might be titanium-nitrided steel, zirconium ceramic coated titanium, or work hardened steel, beta-whitlockite (inorganic hydroxyapatite ceramic). Exemplary soft materials might be commercially pure titanium, silver alloy, low density polyethelene, polyetherether ketone, or bioresorbable polymers commonly known in the art, such as polylactic acid (PLA), polyglycolic acid (PGA), and the like, and copolymers thereof.

In another embodiment, the foil stent could be disposed in a plurality of close-fitting but movable sections (like springs or mesh on the rod surface). The movable sections could be preferentially disposed to improve device interconnections, for example more or less stent material between the screw and rod interface might improve the mechanical strength between the rod and screw.

In an alternative embodiment the density of the stent could be modified such that there is a greater surface area of material disposed near the rod-screw junctions than at the center of the rod in between adjacent rod-screw junctions, thereby providing a localized higher concentration of active agent near the rod-screw junctions. Such a greater surface area of material could be achieved by a finer pitch of the wire foil comprising the stent, or by a larger size of wire foil strut material, or a combination of both. In a preferred embodiment the wire foil stent is deformable along the length of the rod, thereby allowing the surgeon to deformably push the wire foil stent towards the rod-screw junction, thereby creating a local region of increased wire foil density near the rod-screw junction and thus increasing the local concentration of active agent in this region.

Therefore, in accordance with the present invention, there is provided a spinal stabilization system for use in a human spine, comprising:
 a) a spinal rod 1 having a substantially circular outer surface 5,
 b) an annular stent 41 having an inner surface 43 contacting the substantially circular outer surface of the spinal rod,
wherein the annular stent comprises an anti-microbial agent.

Dimensions: The width, depth, or height dimensions of these proposed rod surface features should be controlled to minimize bacterial adherence to a "preferred geometry". It is known that geometric features of certain dimensions enable or promote cell attachment, growth, migration, etc. It might be necessary to perform laboratory experiments to discover if there are similar "micro-geometries" of features that promote or discourage bacterial adherence. Due to the extremely small nature of bacteria, it is unlikely that any surface feature measuring in tens of microns would modulate bacterial behavior, but this should be studied prior to concept implementation.

Subtractive Process for the Coating: From the perspective of coating processing, a rod with a modified surface could be coated with a conventional coating technology, and then the portion of the coating that is not contained within the surface features could be removed from the rod—similar to a mechanical "wiper" system where the coating is stripped from all projecting or peripheral rod surface material but preserved within any recesses of the rod surface. Such a process would preserve bare metal surfaces for metal-on-metal contact with other devices (thereby preserving the mechanics of the uncoated devices). If a coating material creates a slip-plane between two mating surfaces, such a slip-plane is avoided if the coating material is not present on the metallic surfaces making contact. A subtractive coating process might be employed during manufacturing, or it could be employed intraoperatively. The intraoperative coating removal process could be embodied using abrasive materials after the rod is placed into the rod's final pedicle screw position. On the deep rod surface that makes contact with the pedicle screw cap, an abrasive material could be used to remove coating material only in the vicinity of the rod-screw interface. Such an abrasive material might be embodied as a thin strip of material that resides within the pedicle screw head. When this strip of abrasive material is removed after the rod is partially seated (prior to placement of the set-screw), the abrasive strip will remove the rod coating only in the immediate vicinity of the pedicle screw. On the superficial rod surface, an abrasive set-screw could be used to remove the coating material prior to set-screw placement for final rod seating. Such an abrasive set-screw could be a disposable component of the spinal system that is replaced by a final (standard) set-screw, or it could be a novel modified "anti-infective" set-screw.

One way to reduce rod slippage is to improve the set screw/rod interface. A preliminary set screw can be applied that removes the coating only in the area of the set screw. After the preliminary set screw is applied, the final set screw is placed on a rod section where the coating has been removed. Thus, the preliminary set screw would be designed to have a material removal means, such as ridges, cutting teeth or an abrasive material, to remove the coating from the rod surface directly in contact with the set screw. After engaging the preliminary set screw to remove the coating material, the preliminary asset screw would be removed and replaced by the "real" set screw, such as is commonly used in practice without coatings. Alternatively, the material removal means of the set screw could be incorporated into the set screw used for fixation.

In a somewhat analogous manner, the surfaces of the polyaxial screw cap that engage the rod could have a material removal means. Rotating a coated rod in the polyaxial screw cap before locking it into place with a set screw might remove an effective amount of coating material, thereby improving the axial slip strength of the coated rod and screw cap assembly. Similarly, a sheet of abrasive material could be temporarily placed into the polyaxial screw head and removed after the rod was pressed into place. The contact forces between the rod and abrasive sheet would remove the coating thereby preparing a metal surface for screw cap interface.

Thus, mechanical and material design modifications might be required to preserve or enhance the biomechanical properties of spinal constructs created using coated component devices.

Figure 9:
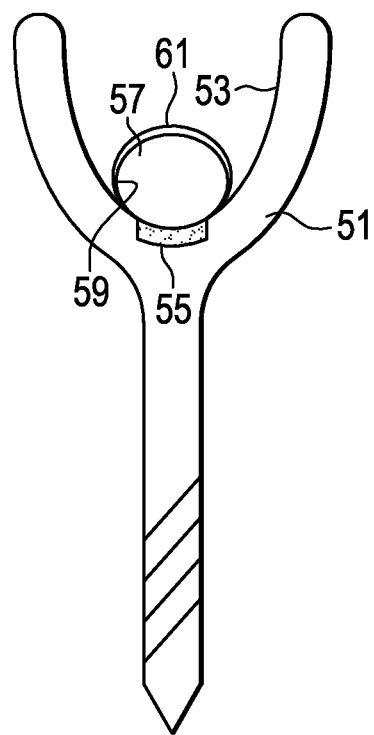
FIG. 9 discloses a spinal stabilization system for use in a human spine, comprising a first bone anchor having a recess for receiving a rod, and a spinal rod having a first end portion having an anti-infective coating thereon.

Therefore, in accordance with the present invention and FIG. 9, there is provided a spinal stabilization system for use in a human spine, comprising:
 a) a first bone anchor 51 having a recess 53 for receiving a rod, wherein at least a portion of the recess comprises an abrasive surface 55, b) a spinal rod 57 having a first end portion 59 having an anti-infective coating 61 thereon, wherein the first end portion of the spinal rod is received in the recess of the first bone anchor.

Selective Deposition Process for the Coating: Preserving metal-on-metal contact might be accomplished by coating selective regions or patterns on the rod surface. For example, stripes of coating material with gaps of uncoated rod surface between the strips might preserve enough metal-contact to eliminate any loss in rod-to-screw interface mechanical strength. Similarly, a discontinuous coating process could be applied where the coating is continuous with discreet uncoated rod surfaces (e.g.—stripes of uncoated rod) contained within the coating or the coating could be discontinuous with the majority of rod surface being uncoated (e.g.—coating dots or strips). Such a coating process could be accomplished by rolling the coating onto the rod or by selectively screening the rod surface from the coating (like a laser-etched shrink-wrap tube). Finally, an electrostatic coating process might concentrate coatings in areas of high charge. Such areas could be defined by micro-machined/deposited "antennas" (like metal spikes or raised surface features) that create local coating densifiers, or prevent the accumulation of applied coatings.

In some embodiments, the coating is applied by a dip coating process.

In some embodiments, the present invention is made with the technology described in U.S. patent application Ser. No. 12/241,503, filed Sep. 30, 2008, entitled "Method for Coating Metallic Surfaces of Medical Devices with an Anti-infective agent" (Chun et al), the specification of which is incorporated by reference in its entirety).

Therefore, in accordance with the present invention, there is provided a spinal rod having a substantially circular outer surface, the outer surface having a coated portion and an uncoated portion, wherein the coated portion contains an anti-microbial agent.

One skilled in the art will appreciate that the rod of the device may be configured for use with any type of bone anchor, e.g., bone screw or hook; mono-axial or polyaxial. Typically, a bone anchor assembly includes a bone screw, such as a pedicle screw, having a proximal head and a distal bone-engaging portion, which may be an externally threaded screw shank. The bone screw assembly may also have a receiving member that is configured to receive and couple a spinal fixation element, such as a spinal rod or spinal plate, to the bone anchor assembly.

The receiving member may be coupled to the bone anchor in any well-known conventional manner. For example, the bone anchor assembly may be poly-axial, as in the present exemplary embodiment in which the bone anchor may be adjustable to multiple angles relative to the receiving member, or the bone anchor assembly may be mono-axial, e.g., the bone anchor is fixed relative to the receiving member. An exemplary poly-axial bone screw is described U.S. Pat. No. 5,672,176, the specification of which is incorporated herein by reference in its entirety. In mono-axial embodiments, the bone anchor and the receiving member may be coaxial or may be oriented at angle with respect to one another. In poly-axial embodiments, the bone anchor may biased to a particular angle or range of angles to provide a favored angle the bone anchor. Exemplary favored-angle bone screws are described in U.S. Patent Application Publication No. 2003/0055426 and U.S. Patent Application Publication No. 2002/0058942, the specifications of which are incorporated herein by reference in their entireties.

Therefore, in accordance with the present invention, there is provided a spinal stabilization system for use in a human spine, comprising:
  a) first and second bone anchors, each anchor having a recess for receiving a rod,
  b) a spinal rod of the present invention, the rod having a first end and a second end portion,
wherein the first end portion of the spinal rod is received in the recess of the first bone anchor, and the second end portion of the spinal rod is received in the recess of the second bone anchor.

We claim:

1. A spinal stabilization system for use in a human spine, comprising:
  a) a bone anchor having a recess for receiving a rod,
  b) a spinal rod having a first end portion, wherein the first end portion of the spinal rod is received in the recess of the bone anchor, and
  c) a first foil disposed between the rod and the recess of the bone anchor,
wherein the first foil comprises an anti-microbial agent,
wherein the first foil comprises perforations, and the anti-microbial agent is present in the perforations.

2. The system of claim 1 wherein the first foil has a first surface, and the anti-microbial agent is present as a coating on the first surface of the foil.

3. The system of claim 1 further comprising:
  d) a second foil disposed between the rod and the recess of the bone anchor,
wherein the second foil comprises an anti-microbial agent.

* * * * *